United States Patent [19]

Morse et al.

[11] 4,107,072

[45] Aug. 15, 1978

[54] PROCESS OF ISOLATING CYCLOHEXANE-FREE ETHYLCELLULOSE MICROCAPSULES

[75] Inventors: Lewis D. Morse, Princeton, N.J.; Melvin J. Boroshok, Yonkers, N.Y.; Roy W. Grabner, North Plainfield, N.J.

[73] Assignee: Merck & Co., Inc., Rahway, N.J.

[21] Appl. No.: 364,222

[22] Filed: May 25, 1973

[51] Int. Cl.$^2$ ............................................. B01J 13/02
[52] U.S. Cl. ..................................... 252/316; 424/35; 427/220; 427/352
[58] Field of Search ................... 252/316; 117/100 A; 424/35; 427/220, 352

[56] References Cited

U.S. PATENT DOCUMENTS

| | | | |
|---|---|---|---|
| 3,155,590 | 11/1964 | Miller et al. | 252/316 X |
| 3,173,878 | 3/1965 | Reyes | 252/316 |
| 3,341,416 | 9/1967 | Anderson et al. | 252/316 X |

*Primary Examiner*—Richard D. Lovering
*Attorney, Agent, or Firm*—Frank M. Mahon; Harry E. Westlake, Jr.; Rudolph J. Anderson, Jr.

[57] ABSTRACT

Ethylcellulose walled microcapsules, obtained from cyclohexane medium are heavily solvated with cyclohexane and tend to form lumps even after drying. Displacements of cyclohexane by pentane, hexane, heptane or octane or mixtures thereof during the isolation of the microcapsules gives a dry product which is essentially all discrete dry microcapsules.

5 Claims, No Drawings

PROCESS OF ISOLATING CYCLOHEXANE-FREE ETHYLCELLULOSE MICROCAPSULES

This invention relates to a process of preparing discrete dry microcapsules. More specifically, it relates to a method of treating ethylcellulose walled microcapsules which have been formed in a cyclohexane medium, by displacing the cyclohexane adhering to the said microcapsules by hexane, in order to obtain essentially all discrete microcapsules with no tendency to lump.

BACKGROUND OF THE INVENTION

A commonly used microencapsulation system involves the release of ethylcellulose from cyclohexane to form a liquid envelop on a solid core, it then is converted into a hard-walled microcapsule. However, when ethylcellulose is precipitated by cooling or coacervation, it comes out solvated with cyclohexane. In such case, the final washed and filtered cakes of microcapsules are difficult to dry. Tray drying leads to dry cakes of microcapsules. Breaking the cakes into lumps, followed by drying, leads to dry lumps of microcapsules. An acceptable solution is to force the microcapsules through screens of progressively smaller mesh opening, and allowing the material to dry between screening. This leads to discrete microcapsules where the microcapsules are large, 60 mesh or larger. With smaller size microcapsules aggregates of dry microcapsules result. Even when fluid bed drying is resorted to, one still gets high yields of lumps or aggregates.

DESCRIPTION OF THE INVENTION

It is an object of this invention to improve the drying methodology of microcapsules to permit the more readily obtaining of discrete dry microcapsules. We have found that this can be achieved by displacing from ethylcellulose capsules, phased out of cyclohexane, the solvated cyclohexane with pentane, hexane, heptane or octane or mixtures thereof such as petroleum ether (i.e., $C_{5-8}$ alkanes). It is an advantage of this invention that the microcapsules thus obtained do not aggregate or clump up and that even very small microcapsules are maintained as discrete dry particles.

The theory of why this invention operates is not known. It is merely an unexplained empirical observation. The nature of the solid core of the microcapsules is irrelevant. The microcapsules can even be blanks with no solid core. The invention applies solely to microcapsules formed with ethylcellulose walls precipitated from cyclohexane. The phasing out can be either by cooling or by polymer/polymer incompatibility as with polyethylene.

The displacement of the cyclohexane by pentane, hexane, heptane or octane can be done in one of several ways. The cyclohexane slurry can be decanted and the residual mass can be reslurried at least once with the pentane, hexane, heptane and/or octane, followed by decanting and then finally filtering. Alternatively, the cyclohexane suspension can be filtered into cake and this can be reslurried at least once in the $C_{5-8}$ alkane and refiltered. It is even possible to wash the filtered cake on the filter with the $C_{5-8}$ alkane. However, this is not recommended as it does not eliminate, in the case of microcapsules formed by coacervation with polyethylene, the small residues of polyethylene which were precipitated.

A very great improvement is observed with one wash by $C_{5-8}$ alkanes; however, more than one wash is generally preferred.

Our invention can be illustrated by the following Examples.

EXAMPLE 1

A typical microencapsulation follows. The internal phase, ascorbic acid, can vary. The amount and type of coating polymer, in this case 10% ethylcellulose based on the final weight of the microcapsules and the amount and type of phasing-out polymer, in this case 25% polyethylene based on the weight of the cellulose, can all vary.

The following were dispersed in 18.75 liters cyclohexane, using a turbine impeller and baffles:

450 gm. Ethylcellulose (47.5% ethoxy content by weight; viscosity 100 cps at 25° C as a 5% by weight solution in a 80:20 toluene:ethanol mixture).

112.5 gm. Polyethylene granules (molecular weight about 7,000).

4050 gm. Ascorbic Acid, 100 mesh size range.

The system was stirred with heating. At 80° C both the ethylcellulose and the polyethylene had dissolved in the cyclohexane.

Stirring was continued while the system was allowed to cool. As the temperature dropped, solvated ethylcellulose developed as a separate phase due to the presence of the polyethylene. This is a known art, described in the literature as an example of coacervation resulting from polymer/polymer incompatibility. The solvated ethylcellulose, distributed in the cyclohexane as droplets by the turbine, tended to wet the ascorbic acid particles and to envelope them. As the temperature dropped further, the ethylcellulose lost solvent and developed into solid encapsulating walls. The continuous phase, cyclohexane, contained minute particles of polyethylene; at 45° C the walls had stopped building up. 5.75 Liters cold cyclohexane was poured off together with the minute particles of polyethylene. The microcapsules were resuspended in five liters clean cyclohexane. This was continued two more times until the capsules were washed clean of polyethylene and other debris.

The microcapsule cake was spread onto filter paper in a hood, breaking up the cake with a spatula. The clumps that resulted were broken further as the microcapsules dried.

The final product when examined under the microscope showed very few discrete microcapsules. Most of the dried particles consisted of several microcapsules aggregated to a tough unit. Microscopically, the batch contained a high proportion of lumps up to 5 mm in diameter.

EXAMPLE 2

The microcapsules of Example 1 were washed with cyclohexane as in Example I and then the cake was squeezed to a damp condition through a cloth after each wash.

The final damp cake, containing about 50% solids was forced through a 10 mesh screen two times. This was really an extrusion since the damp particles came through the openings as strands that broke up. Because of the drying that took place throughout the process, the cake actually sieved through the openings on the third pass, as 10 mesh lumps.

The 10-mesh lumps were forced through a 20-mesh screen, and then sieved through the 20-mesh screen and spread to dry.

The resultant capsules, with a theoretical 80% vitamin content, when screened through standard Taylor sieves, were:

| On Sieve No. | % (w/w) |
|---|---|
| 12 | Trace |
| 16 | 1.4 |
| 20 | 2.4 |
| 30 | 5.1 |
| 40 | 9.2 |
| 60 | 54.0 |
| 80 | 20.2 |
| 100 | 5.0 |
| 140 | 2.1 |
| 200 | 0.1 |
| 325 | 0.1 |
| pan | 0.0 |

EXAMPLE 3

The microcapsules of Example I were washed once with cyclohexane as in Example 2, but the last two washes were with hexane.

The cake sieved through a 20-mesh screen immediately with no previous extrusion through 10 or 20 mesh sieves.

The final product had essentially the same sieve analysis as that of Example 2.

EXAMPLE 4

The cake of Example I, was dried in a Glatt fluid bed drier, 5 kg. capacity.

The air flow, or velocity, is controlled by a lever that has a pointer on a scale of 1 to 7. The cake was dried for the first ten minutes at 1-½ on the scale, and at ½ on the scale for the balance of 30 minutes. To help break up the cake, the lever was jerked suddenly from 1-½ to 7. This gave the cake a jolt, tending to disrupt the cake. This jolting action was employed several times during the first ten minutes.

The resultant product consisted of an estimated 25–50% discrete microcapsules. The balance was lumpy. The lumps ranged in size from 1 inch to ¼ inch. They were not fragile but tough.

EXAMPLE 5

The cake of Example 3 was dried in a fluid bed drier as in Example 4. The resultant product consisted of discrete microcapsules with a sieve analysis as follows:

| On Sieve No. | % (w/w) |
|---|---|
| 12 | 0 |
| 16 | 0 |
| 20 | 0.1 |
| 30 | 0.3 |
| 40 | 0.5 |
| 60 | 15.2 |
| 80 | 40.3 |
| 100 | 21.8 |
| 140 | 13.7 |
| 200 | 5.8 |
| 325 | 1.0 |
| pan | 0.1 |

EXAMPLE 6

Thiamine mononitrate was microencapsulated as in Example I, using the formula:

Cyclohexane — 5 liters
Thiamine Mononitrate (30–80) — 775 gm.
Ethylcellulose — 180 gm.
Polyethylene — 45 gm.
The batch was quenched with one liter cyclohexane.

The cake was washed once with 2 liters cyclohexane. Then the cake was divided into parts A and B. A was washed with a liter of cyclohexane and then with a liter of hexane. B was washed two times, each time with one liter of hexane. The two were dried on a Glatt fluid bed drier.

A yielded 403 gm. product with 0.62% on 10 mesh.

B yielded 499 gm. product with 0.30% on 10 mesh.

Thus, either method of hexane treatment is effective.

EXAMPLE 7

A remarkable aspect of hexane washing is its effect even with very fine microcapsules. Ferrous sulfate, dried, with particles in the 10–30 micron range, was microencapsulated as in Example 6, using the formula:
Cyclohexane — 5 liters
Ferrous Sulfate — 775 grams
Ethylcellulose — 180 grams
Polyethylene — 45 grams
The cake was washed as Example 6, method B.

Product consisted of discrete capsules, with less than ½% on 10 mesh, 45 gm. on 100 mesh and 805 gm. through 100 mesh. The larger particles were discrete microcapsules but each microcapsule contained more than one ferrous sulfate particle.

EXAMPLE 8

Example 6 was scaled up to 50-gallon kettle in the pilot plant, using the old straight cyclohexane wash. This yielded product with many large lumps. An estimated 25% of the product consisted of discrete microcapsules.

EXAMPLE 9

Example 6 was scaled up to a 50-gallon kettle in the pilot plant, using the new hexane wash (as in Example 6, method B). The product consisted of all discrete microcapsules except for a trace of agglomerated material.

EXAMPLE 10

Example 9 was scaled up to a 1000 gal. kettle. A filter pot was used for washing. One third of the batch was washed at a time and dried immediately in an Aeromatic fluid bed drier.

The product consisted of essentially all discrete microcapsules.

EXAMPLE 11

The following are dispersed in 5 liters cyclohexane:
280 gm. Ethylcellulose (47.5% ethoxy content by weight; viscosity 45 cps)
520 gm. Niacinamide
The mixture is heated with stirring to 78° C. At that temperature the ethylcellulose has dissolved in the cyclohexane. Stirring is continued while the system is allowed to cool. As the temperature drops solvated ethylcellulose develops as a separated phase due to the poor solvent characteristics of cyclohexane at lower temperatures (Cf. U.S. Pat. No. 3,531,418). The solvated ethylcellulose, distributed in the cyclohexane as droplets, tend to wet the niacinamide particles and to envelope them. As the droplets coalesce, lose solvent and develop into solid encapsulating walls. Cool to 10°

C and filter. Wash twice with 1.5 liters hexane. Dry in a fluid bed to achieve discrete capsules as a free flowing powder.

EXAMPLE 12

The procedure of Example 11 is used substituting pentane for hexane. The results are the same as in Example 11.

EXAMPLE 13

The procedure of Example 11 is used substituting heptane for hexane. The results are the same as in Example 11.

EXAMPLE 14

The procedure of Example 11 is used substituting octane for hexane. The results are the same as in Example 11.

We claim:

1. In the process of isolating ethylcellulose-walled microcapsules from a cyclohexane medium, the improvement which comprises displacing the cyclohexane adhering to the said microcapsules by $C_{5-8}$ alkanes.

2. The process of claim 1 in which the alkane is hexane.

3. The process of claim 2 in which said displacement of cyclohexane is achieved by at least one washing of the hardened microcapsules with hexane after separation of said capsules from most of the liquid cyclohexane.

4. The process of claim 3 in which the cyclohexane in which said capsules are formed is decanted and the residual case is stirred at least once with hexane.

5. The process of claim 2, in which said displacement of cyclohexane is carried out by washing a filter cake of said capsules, at least once with hexane.

* * * * *